US012600718B2

(12) United States Patent
Sun et al.

(10) Patent No.: US 12,600,718 B2
(45) Date of Patent: Apr. 14, 2026

(54) METHOD FOR PREPARING COMPOUND AS PI3K INHIBITOR AND INTERMEDIATE COMPOUND FOR PREPARING SAME

(71) Applicant: BORYUNG CORPORATION, Seoul (KR)

(72) Inventors: Yong Ho Sun, Gunpo-si (KR); Ok Kyoung Choi, Siheung-si (KR); Joon Kwang Lee, Gwangmyeong-si (KR); Ji Han Kim, Seoul (KR)

(73) Assignee: BORYUNG CORPORATION, Seoul (KR)

( * ) Notice: Subject to any disclaimer, the term of this patent is extended or adjusted under 35 U.S.C. 154(b) by 557 days.

(21) Appl. No.: 18/013,801

(22) PCT Filed: Jun. 29, 2021

(86) PCT No.: PCT/KR2021/008200
§ 371 (c)(1),
(2) Date: Dec. 29, 2022

(87) PCT Pub. No.: WO2022/005175
PCT Pub. Date: Jan. 6, 2022

(65) Prior Publication Data

US 2023/0295158 A1 Sep. 21, 2023

(30) Foreign Application Priority Data

Jun. 30, 2020 (KR) ........................ 10-2020-0080269

(51) Int. Cl.
*C07D 471/04* (2006.01)
*C07D 401/12* (2006.01)

(52) U.S. Cl.
CPC ......... *C07D 471/04* (2013.01); *C07D 401/12* (2013.01)

(58) Field of Classification Search
None
See application file for complete search history.

(56) References Cited

U.S. PATENT DOCUMENTS

| | | | |
|---|---|---|---|
| 2007/0004705 A1 | 1/2007 | Brasca et al. | |
| 2015/0291593 A1 | 10/2015 | Su et al. | |
| 2015/0307520 A1 | 10/2015 | Su et al. | |
| 2018/0105527 A1 | 4/2018 | Lee et al. | |

FOREIGN PATENT DOCUMENTS

| | | | |
|---|---|---|---|
| CN | 1726217 | 1/2006 | |
| CN | 104151311 | 11/2014 | |
| EP | 1277738 | 1/2003 | |
| KR | 10-2016-015006 | 12/2016 | |
| KR | 10-2016-0150006 | 12/2016 | |
| KR | 20160150006 A * | 12/2016 | ................ A61P 5/14 |
| TW | 201404779 | 2/2014 | |
| WO | 2004048365 | 6/2004 | |
| WO | 2009/099801 | 8/2009 | |
| WO | 2010151740 | 12/2010 | |
| WO | 2011/053861 | 5/2011 | |
| WO | 2014015523 | 1/2014 | |
| WO | 2014015675 | 1/2014 | |
| WO | 2014167347 | 10/2014 | |

OTHER PUBLICATIONS

Welker et al. "Recent syntheses of PI3K/Akt/mTOR signaling pathway inhibitors", Bioorganic & Medicinal Chemistry 21 4063-4091. (Year: 2013).*
Komkov et al. "Synthesis of new trichloromethyl- and alkoxy-substituted pyrido[2,3-d]pyrimidine derivatives", Russian Chemical Bulletin, International Edition, vol. 68, No. 2, pp. 365-373. (Year: 2019).*
Tetsuzo Kato et al., "Studies on Ketene and Its Derivatives. KIX[1]) Ring-Closure of 5-Acetyl-2,6-dimethyl-4(3H)-pyrimidone", Yakugaku Zasshi, 1973, vol. 93, No. 12, pp. 1685-1687.
A.V. Komkov et al., "Synthesis of new trichloromethyl- and alkoxy-substituted pyrido[2,3-d]pyrimidine derivatives", Russian Chemical Bulletin, International Edition, Feb. 2019, vol. 68, No. 2, pp. 365-373.
International Search Report dated Oct. 6, 2021, for PCT/KR2021/008200, 9 pp.
Written Opinion of the ISA dated Oct. 6, 2021, for PCT/KR2021/008200, 9 pp.
Dai et al., "Progress in clinical study of Phosphatidyl Inositol 3-Kinase Inhibitors as anticancer Agents", Strait Pharmaceutical Journal, vol. 26, No. 6., 2014, pp. 6-13.
Myers et al., "Protective Groups—Silicon-Based Protection of the Hydroxyl Group", Chem 115, Nov. 11, 1999, 26 pages.
Yoon et al., "Efficient Synthesis of 4,5,6-Trisubstituted-2-aminopyrimidines", Bull. Korean Chem. Soc. 2009, vol. 30, No. 9, May 14, 2009, pp. 2107-2110.
Lockner, "Stoichiometric Enamine Chemistry", Baran Group Meeting, Nov. 3, 2007, 8 pages.

* cited by examiner

*Primary Examiner* — Susan T Tran
(74) *Attorney, Agent, or Firm* — NIXON & VANDERHYE, PC

(57) ABSTRACT

The present invention provides a method for preparing a compound as a PI3K inhibitor with reduced process steps, including a process that has a shortened reaction time in the preparation of the compound as a PI3K inhibitor, and enabling reaction in mild conditions. Accordingly, the present invention provides a method for preparing a compound as a PI3K inhibitor, which is easy in process management and industrial mass-production while achieving process simplification, compared to existing known preparation methods.

17 Claims, No Drawings

METHOD FOR PREPARING COMPOUND AS PI3K INHIBITOR AND INTERMEDIATE COMPOUND FOR PREPARING SAME

CROSS-REFERENCE TO RELATED APPLICATIONS

This application is the U.S. national phase of International Application No. PCT/KR2021/008200 filed Jun. 29, 2021, which designated the U.S. and claims priority to KR 10-2020-0080269 filed Jun. 30, 2020, the entire contents of each of which are hereby incorporated by reference.

TECHNICAL FIELD

The present invention relates to a method for preparing a compound as a PI3K inhibitor and an intermediate compound for preparing the same.

BACKGROUND ART

Phosphatidylinositol 3-kinase (PI3 kinase; PI3K) is a lipid kinase, which phosphorylates lipid molecules instead of proteins, and plays an important role in cell survival, signal transduction, control of membrane trafficking, etc. If a problem occurs to a control thereof, cancer, inflammatory diseases, autoimmune diseases, etc. occur.

Recently, there has been a report on research results for developing a compound having a structure capable of selectively inhibiting PI3 kinase. The compound as a PI3K inhibitor may be advantageously used for treating cancer, autoimmune diseases, respiratory diseases and the like. Accordingly, simplifying a process in the preparation of the compounds as the PI3K inhibitor has emerged as an important issue.

DETAILED DESCRIPTION OF THE INVENTION

Technical Problem

One object of the present invention is to provide a novel method for preparing a compound as a PI3K inhibitor, which enables process simplification.

One object of the present invention is to provide a method for preparing an intermediate compound for preparing a compound as a PI3K inhibitor, which enables process simplification.

One object of the present invention is to provide an intermediate compound for preparing a compound as a PI3K inhibitor, which enables process simplification.

Technical Solution

To solve the above problems, the present invention may provide a method for preparing a compound of formula 7. The method for preparing the compound of formula 7 may include:

(S1) preparing a compound of formula 5 from a compound of formula 4;

(S2) reacting the compound of formula 5 with dimethylformamide-dimethylacetal to prepare a compound of formula 6; and (S3) subjecting the compound of formula 6 to a cyclization reaction to prepare a compound of formula 7.

[Formula 4]

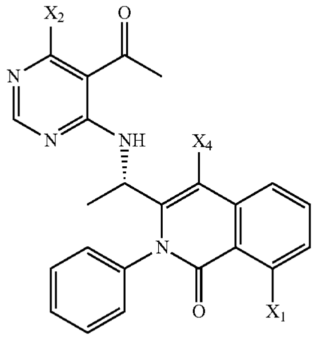

[Formula 5]

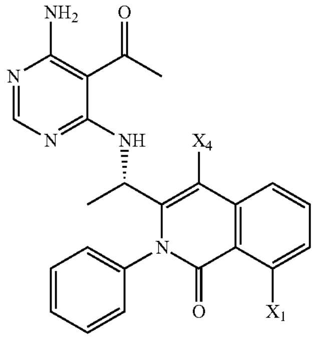

[Formula 6]

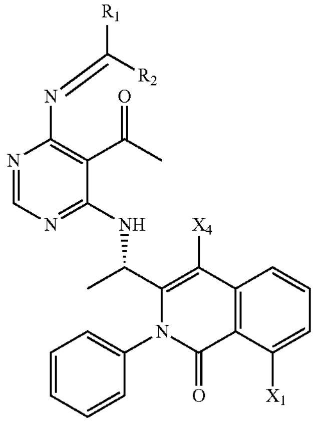

[Formula 7]

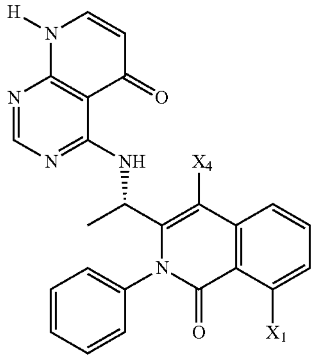

In above formulas 4 to 7, $X_1$, $X_2$ and $X_4$ may be each independently a halogen atom.

Above $X_1$, $X_2$ and $X_4$ may be the same or different from each other. $X_1$, $X_2$ and $X_4$ may be each independently F, Cl, Br or I. More specifically, above $X_1$, $X_2$ and $X_4$ may be each independently Br or Cl. For example, $X_1$, $X_2$ and $X_4$ may be all Cl. Above $X_1$ and $X_4$ may be Cl.

In above formula 6, any one of $R_1$ and $R_2$ may be a hydrogen atom and the other may be dimethylamine.

The method for preparing the compound of formula 7 may further include (S1-1) subjecting a compound of formula 3 to a halogenation reaction to prepare the compound of formula 4.

[Formula 3]

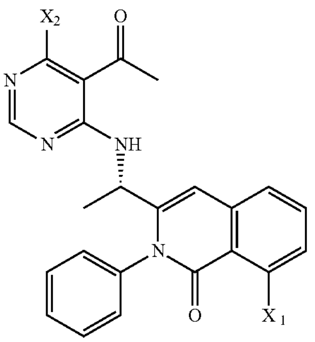

In above formula 3, $X_1$ and $X_2$ may be the same as defined in above formulas 4 to 7.

The method for preparing the compound of formula 7 may further include (S1-2) reacting a compound of formula 1 with a compound of formula 2 to prepare the compound of above formula 3.

[Formula 1]

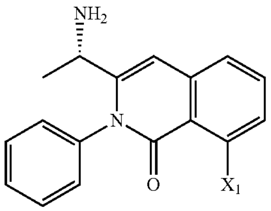

[Formula 2]

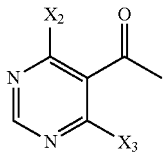

In above formulas 1 and 2, $X_1$ and $X_2$ may be each independently the same as defined in above formulas 4 to 7. In above formula 2, $X_3$ may be a halogen atom.

The halogen atom may be any one selected from F, Cl, Br, or I, unless otherwise specified herein. For example, the halogen atom may be any one selected from Cl and Br.

The method for preparing the compound as the PI3K inhibitor may include (S1) to (S3) below:

(S1) subjecting the compound of formula 4 to amination to prepare the compound of formula 5;

(S2) reacting the compound of formula 5 with dimethylformamide-dimethylacetal to prepare the compound of formula 6; and (S3) subjecting the compound of formula 6 to a cyclization reaction to prepare the compound of formula 7.

The method for preparing the compound as the PI3K inhibitor may further include (S1-1) below:

(S1-1) subjecting the compound of formula 3 to a halogenation reaction to prepare the compound of formula 4.

The method for preparing the compound as the PI3K inhibitor may further include (S1-2) below:

(S1-2) reacting the compound of formula 1 with the compound of formula 2 to prepare the compound of formula 3.

The method for preparing the compound of formula 7 according to one embodiment may include:

(S1-2) reacting the compound of formula 1 with the compound of formula 2 to prepare the compound of formula 3;

(S1-1) subjecting the compound of formula 3 to a halogenation reaction to prepare the compound of formula 4;

(S1) preparing the compound of formula 5 from the compound of formula 4;

(S2) reacting the compound of formula 5 with dimethylformamide-dimethylacetal to prepare the compound of formula 6; and (S3) subjecting the compound of formula 6 to a cyclization reaction to prepare the compound of formula 7. Matters mentioned about the compounds of formulas 1 to 7 may be equally applied, if not contradictory to each other.

In addition, the method for preparing the compound of formula 7 according to one embodiment may include:

(S1-2) reacting the compound of formula 1 with the compound of formula 2 to prepare the compound of formula 3;

(S1-1) subjecting the compound of formula 3 to a halogenation reaction to prepare the compound of formula 4;

(S1) subjecting the compound of formula 4 to amination to prepare the compound of formula 5;

(S2) reacting the compound of formula 5 with dimethylformamide-dimethylacetal to prepare the compound of formula 6; and (S3) subjecting the compound of formula 6 to a cyclization reaction to prepare the compound of formula 7. Matters mentioned about the compounds of formulas 1 to 7 may be equally applied, if not contradictory to each other.

Above (S1) may be performed in a polar aprotic solvent. For example, the solvent of above (S1) may include dimethylsulfoxide. Above (S1) may be performed under a basic condition. For example, in above (S1), a basic compound such as ammonium hydroxide may be involved in a reaction.

Above (S1-2) may be performed in a polar aprotic solvent. For example, the solvent of above (S1-2) may include acetonitrile. Above (S1-2) may be performed under a basic condition. For example, in above (S1-2), a basic compound may be involved in a reaction. The basic compound may be, for example, a tertiary amine such as triethylamine.

In the present specification, the polar aprotic solvent may include at least one of dichloromethane, tetrahydrofuran, ethyl acetate, dimethyl sulfoxide, dimethylformamide, and acetonitrile, but is not limited thereto.

In above (S1-2), an equivalent ratio of the compound of above formula 1, the compound of above formula 2 and the triethylamine may be 1:1.1:1.5.

Above $X_1$ and $X_2$ may be Cl.

More specifically, above (S1-2) may include: adding the compound of above formula 1 and the compound of above formula 2 to an organic solvent (for example, a mixed solvent of acetonitrile and triethylamine), and refluxing and stirring for about one to three hours; cooling to room temperature, adding purified water, and stirring at room temperature; filtering and washing (for example, a washing solvent may be purified water); and drying.

Above (S1-1) may be reacting the compound of above formula 3 with N-chlorosuccinimide to perform a chlorination reaction. In (S1-1), an equivalent ratio of the compound of above formula 3 and above N-chlorosuccinimide may be 1:1.13.

Above (S1-1) may be performed in a polar aprotic solvent. More specifically, above (S1-1) may be performed in at least one solvent selected from dichloromethane and acetonitrile.

More specifically, above (S1-1) may include: adding the compound of formula 3 and N-chlorosuccinimide to an organic solvent (for example, dichloromethane), and refluxing and stirring for about three hours; cooling to room temperature, concentrating, adding an organic solvent (for example, acetonitrile), and re-concentrating; adding acetonitrile, cooling to about 0° C. or more and 5° C. or less and stirring; filtering and washing (a washing solvent used herein may be an organic solvent, for example, acetonitrile); and drying.

Above (S1) may include reacting the compound of above formula 4 with ammonium hydroxide ($NH_4OH$) to produce a crude product of formula 5. Above (S1) may include purifying the crude product.

The purifying of the crude product may include at least one selected from ethanol, isopropyl alcohol, and acetone as a purification solvent. In the purifying of the crude product, isopropyl alcohol may be used as the purification solvent.

In above (S1), an equivalent ratio of the compound of above formula 4 and ammonium hydroxide ($NH_4OH$) may be 1:5 to 1:15.

More specifically, in above (S1), the producing of the crude product may include: adding the compound of above formula 4 and ammonium hydroxide ($NH_4OH$) to an organic solvent (for example, dimethyl sulfoxide), raising a temperature (about 70° C. to 90° C., for example, about 80° C.) for about three hours, and stirring; stirring at room temperature for about one to two hours (or for about two hours or more until a solid is produced), adding purified water, and stirring again at room temperature; filtering and washing (a washing solvent used herein may be purified water); and drying.

More specifically, in above (S1), the purifying of the crude product may include: adding an organic solvent (for example, isopropyl alcohol) to the crude product, refluxing and stirring for about 30 minutes; stirring at room temperature for about one to two hours; filtering and washing (a washing solvent used herein may be an organic solvent, for example, isopropyl alcohol); and drying.

In above (S2), an equivalent ratio of the compound of above formula 5 and above dimethylformamide-dimethylacetal may be 1:2.

More specifically, above (S2) may include: refluxing and stirring the compound of formula 5 and dimethylformamide-dimethylacetal in an organic solvent (for example, dichloromethane) for about one hour; cooling to room temperature and concentrating; adding an organic solvent (for example, isopropyl alcohol), refluxing, and stirring; cooling to room temperature and stirring; filtering and washing (a washing solvent used herein may be an organic solvent, for example, isopropyl alcohol); and drying.

In above (S3), the cyclization reaction may include reacting the compound of above formula 6 with a base and adding an acid. The adding of the acid may be performed after reacting the compound of above formula 6 with the base. The base may be a tert-butoxide salt. For example, the base may be potassium tert-butoxide or sodium tert-butoxide. The acid may be an organic acid or an inorganic acid, for example, acetic acid or hydrochloric acid.

In above (S3), an equivalent ratio of the compound of above formula 6 and the base may be 1:1.5. An equivalent ratio of the compound of above formula 6 and the acid may be 1:3.

More specifically, above (S3) may include: adding the compound of formula 6 to an organic solvent (for example, a mixed solvent of tetrahydrofuran and acetonitrile), cooling to about −5° C., and stirring; adding portionwise (for example, about two to three times) of the base, cooling and stirring for about 30 minutes to two hours; adding purified water, adding an acid (for example, acetic acid) dropwise to produce a solid, and stirring at room temperature for about one to two hours; filtering and washing (a washing solvent used herein may be purified water); and drying.

In one embodiment, the method for preparing the compound of formula 7 may further include purifying a crude product of the compound of formula 7.

In addition, the present invention may provide the method for preparing the compound of formula 6. The method for preparing the compound of formula 6 according to one embodiment may include reacting the compound of formula 5 with dimethylformamide-dimethylacetal.

[Formula 5]

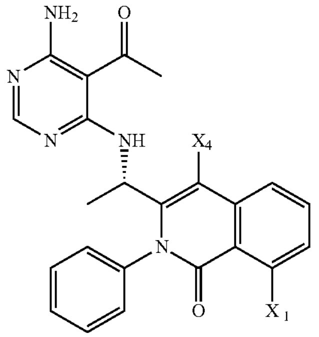

[Formula 6]

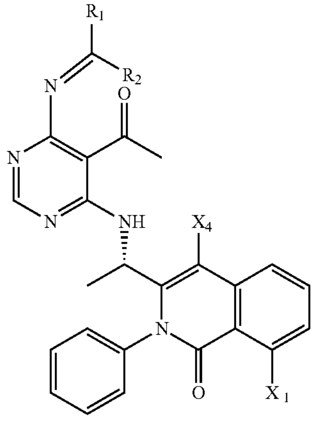

In above formulas 5 and 6, $X_1$ and $X_4$ may be each independently a halogen atom. In above formula 6, any one of $R_1$ and $R_2$ may be a hydrogen atom and the other may be dimethylamine.

The method for preparing the compound of above formula 6 may provide the compound of formula 6 which is an intermediate compound used in the process for preparing the compound of formula 7 of the present invention, thereby reducing the process steps for preparing the compound of formula 7 and reducing a process time.

The method for preparing the compound of formula 7 according to one embodiment may include subjecting the compound of formula 6 described above to a cyclization reaction.

According to one embodiment of the present invention, the compound represented by formula 6 below may be provided.

[Formula 6]

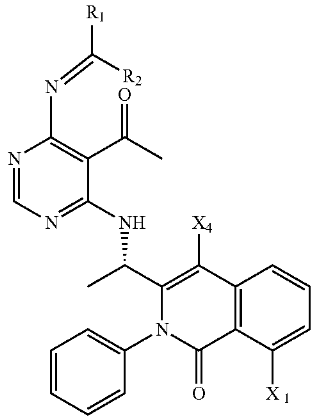

In above formula 6, $X_1$ and $X_4$ may be each independently a halogen atom. Any one of $R_1$ and $R_2$ may be a hydrogen atom and the other may be dimethylamine.

The compound represented by above formula 6 may be involved as an intermediate compound in the process of preparing the compound as the PI3K inhibitor of one embodiment, thereby reducing process steps and process costs.

According to the present invention, unlike the conventionally known method for preparing the compound as the PI3K inhibitor, the process steps required for preparing the compound as the PI3K inhibitor may be reduced, and the compound may be synthesized as the PI3K inhibitor without long reflux and stirring reactions, which take several days or more. In addition, a reaction may be performed under mild reaction conditions, and thus risk factors which may occur during synthesis may be remarkably reduced, and a preparation process may be easily managed.

Thus, process simplification may be achieved to shorten a time required for process, with less process costs and easy process management. Accordingly, the method for preparing the compound as the PI3K inhibitor according to one embodiment may be suitable for industrial production of the compound as the PI3K inhibitor.

Advantageous Effects

According to a method for preparing a compound as a PI3K inhibitor of the present invention, it is possible to simplify a preparation process of a compound as a PI3K inhibitor, thereby reducing preparation steps and costs. In addition, an intermediate compound for the preparation of the compound as the PI3K inhibitor according to the present invention may be used in the preparation process of the compound as the PI3K inhibitor, thereby reducing preparation steps and costs. Accordingly, the productivity of the compound as the PI3K inhibitor may be improved.

BEST MODE FOR INVENTION

Hereinafter, the advantages and features of the present invention and methods for achieving the same will be described in detail with reference to the following exemplary embodiments. However, the present invention is not limited to the exemplary embodiments disclosed hereinafter, but will be implemented in various different forms. Hereinafter, the following exemplary embodiments will be suggested for better understanding of the present invention and are provided only for the purpose of completely illustrating the scope of the present invention to those skilled in the art, and thus the present invention will be defined only by the scope of the claims thereto.

Example 1: Synthesis of (S)-4-((1-(4,8-dichloro-1-oxo-2-phenyl-1,2-dihydroisoquinolin-3-yl)ethyl)amino)pyrido[2,3-d]pyrimidin-5(8H)-one 1. Scheme

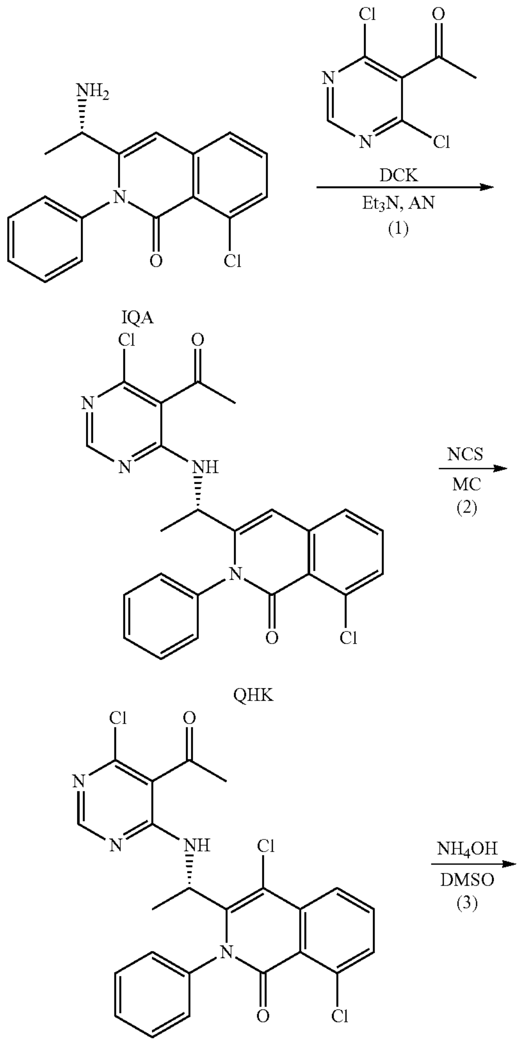

IQA

QHK

IQCK

-continued

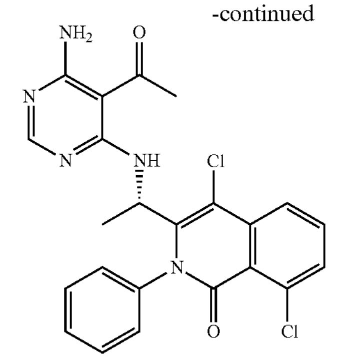

IQNK

DMF-DMA
MC
(4)

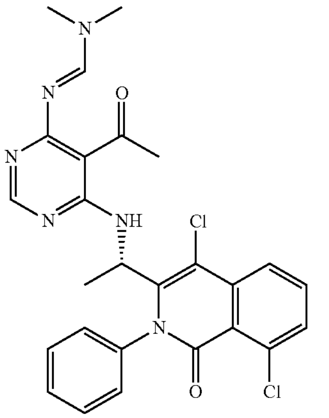

KOtBu
THF, ACN
(5)

or

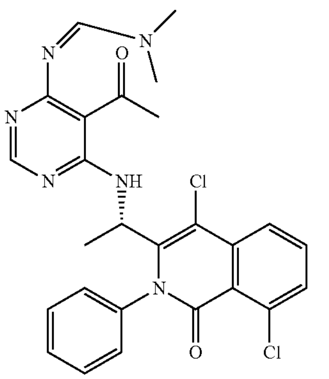

IQVK

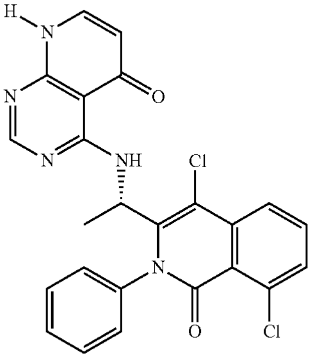

2. Step (1)—Synthesis of Intermediate Compound QHK

Acetonitrile (AN, 80 ml), DCK (1-(4,6-dichloropyrimidin-5-yl)ethenone, 7.0 g, 36.8 mmol) and triethylamine ($Et_3N$, 7.0 ml, 50.2 mmol) were added to an intermediate compound IQA ((S)-3-(1-aminoethyl)-8-chloro-2-phenylisoquinolin-1(2H)-one, 10 g, 33.5 mmol) according to the above scheme and stirred under reflux for three hours. After cooling to room temperature (25° C.), purified water (20 ml) was added thereto and stirred at room temperature (25° C.). The resulting solid was filtered, washed with purified water (25 ml), and dried with hot air at 40° C. to obtain an intermediate compound QHK ((S)-3-(1-((5-acetyl-6-chloropyrimidin-4-yl)amino)ethyl)-8-chloro-2-phenylisoquinolin-1(2H)-one). (13.8 g, yield: 91%).

$^1$H-NMR (400 MHz, $CDCl_3$): δ 1.43 (d, 3H), δ 2.78 (s, 3H), δ 4.92 (t, 1H) δ 6.48 (s, 1H), δ 7.26-7.46 (m, 8H), δ 8.18 (s, 1H), δ 8.97 (d, 1H).

3. Step (2)—Synthesis of Intermediate Compound IQCK

Dichloromethane (MC, 35 ml) and N-chlorosuccinimide (NCS, 2.0 g, 15 mmol) were added to the intermediate compound QHK (6.0 g, 13 mmol) obtained in above step (1), and stirred under reflux for three hours. After cooling to room temperature (25° C.), the reaction mixture was concentrated under reduced pressure. Acetonitrile (18 ml) was added to the concentrated residue, cooled and stirred at 0-5° C. for one hour, after which the solid was filtered, washed with acetonitrile (6 ml), and dried with hot air at 40° C. to obtain an intermediate compound IQCK ((S)-3-(1-((5-acetyl-6-chloropyrimidin-4-yl)amino)ethyl)-4,8-dichloro-2-phenylisoquinolin-1(2H)-one). (5.7 g, yield: 89%)

$^1$H-NMR (400 MHz, $CDCl_3$): δ 1.62 (d, 3H), δ 2.74 (s, 3H), δ 4.98 (t, 1H), δ 7.17-7.95 (m, 8H), δ 8.26 (s, 1H), δ 9.37 (broad, 1H)

4. Step (3)—Synthesis of Intermediate Compound IQNK

Dimethylsulfoxide (DMSO, 304 ml) and ammonium hydroxide (48.6 ml, 642 mmol) were added to the intermediate compound IQCK (30.4 g, 62 mmol) obtained in above step (2), and then heated and stirred at 80° C. for five hours, cooled to room temperature, and stirred overnight. Purified water (304 ml) was added to the reaction mixture in which the solid was formed, and the mixture was further stirred at room temperature for 1.5 hours. The solid of the reaction mixture was filtered, washed with purified water (610 ml), and dried with hot air at 40° C. to obtain a crude product of IQCK (29.8 g). The crude product of IQNK (29.8 g) was added in isopropyl alcohol (300 ml) and stirred under reflux for 10 minutes, cooled to room temperature, and further stirred for two hours. The resulting solid was filtered, washed with isopropyl alcohol (75 ml), and dried with hot air at 40° C. to obtain the purified IQNK ((S)-3-(1-((5-acetyl-6-aminopyrimidin-4-yl)amino)ethyl)-4,8-dichloro-2-phenylisoquinolin-1(2H)-one). (26.9 g, yield 92%)

$^1$H-NMR (400 MHz, $CDCl_3$): δ 1.60 (d, 3H), δ 2.56 (s, 3H), δ 5.03 (t, 1H), δ 5.77 (br, 2H), δ 7.15-7.97 (m, 9H)

Although isopropyl alcohol was used as a solvent for the purification of the crude product of IQNK in above step (3), the examples are not limited thereto, and it is needless to say that various organic solvents may be used. For example, any one or more organic solvents selected from ethanol, isopropyl alcohol, and acetone may be used. Preferably, an isopropyl alcohol solvent may be used.

5. Step (4)—Synthesis of Intermediate Compound IQVK

Dichloromethane (130 ml) and dimethylformamide-dimethylacetal (DMF-DMA, 15.2 ml, 114.4 mmol) were added to the intermediate compound IQNK (26.8 g, 57.2 mmol) obtained in above step (3), stirred under reflux for one hour, cooled to room temperature (25° C.), and concentrated under reduced pressure. Isopropyl alcohol (190 ml) was added to the concentrated residue, stirred under reflux, and cooled to room temperature, after which the solid was filtered. The filtered solid was washed with isopropyl alcohol (80 ml) and dried with hot air at 40° C. to obtain an intermediate compound IQVK ((S)—N'-(5-acetyl-6-((1-(4,8-dichloro-1-)oxo-2-phenyl-1,2-dihydroisoquinolin-3-yl)ethyl)amino)pyrimidin-4-yl)-N,N-dimethylformimidamide). (26.2 g, yield: 88%)

$^1$H-NMR (400 MHz, $CDCl_3$): δ 1.60 (d, 3H), δ 2.75 (s, 3H), δ 3.11 (s, 3H), δ 3.14 (s, 3H), δ 4.99 (t, 1H), δ 7.26-7.96 (m, 8H), δ 8.10 (s, 1H), δ 8.55 (s, 1H)

6. Step (5)—Synthesis of Final Product

Tetrahydrofuran (6 ml) was added to the intermediate compound IQVK (1 g, 1.9 mmol) obtained in above step (4), and cooled and stirred at −5° C. Potassium tert-butoxide (0.32 g, 2.9 mmol) was added portionwise three times and stirred while maintaining a temperature at −5° C. for 0.5 hours, after which purified water (12 ml) was added, and acetic acid (0.33 ml, 5.7 mmol) was added, and then stirred at room temperature for two hours. The resulting solid was filtered, washed with purified water (10 ml), and dried with hot air at 40° C. to obtain the final product ((S)-4-((1-(4,8-dichloro-1-oxo-2-phenyl-1,2-dihydroisoquinolin-3-yl) ethyl)amino)pyrido[2,3-d]pyrimidin-5(8H)-one) (0.85 g, yield: 77%).

$^1$H-NMR (400 MHz, $CDCl_3$): δ 1.67 (d, 3H), δ 5.03 (t, 1H), δ 6.31 (d, 1H), δ 7.20-7.95 (m, 9H), δ 8.25 (s, 1H)

Referring to Example 1, in the method for preparing the compound as the PI3K inhibitor according to one example, the compound as the PI3K inhibitor may be synthesized through only five steps from steps (1) to (5). In addition, since a reaction time for each step is short, a process time may be shortened. More specifically, steps (1) to (5) may not have stress reaction conditions which require refluxing and stirring for several days or more. In particular, steps (1) to (5) may include the refluxing and stirring steps for about one to about five hours or so, and may not include the refluxing and stirring steps which take longer than those hours. Thus, the total working days may be shortened by several days or more according to the method for preparing the compound as the PI3K inhibitor of one example. In addition, since a strong acid such as trifluoroacetic acid (TFA) or methanesulfonic acid (MsOH) is not used, a reaction may proceed under mild reaction conditions. Accordingly, risk factors which may occur during synthesis may be remarkably reduced, and a preparation process may be easily managed.

In the method for preparing the PI3K inhibitor according to one example, the PI3K inhibitor may be prepared by a preparation method including steps (S1) to (S5), so as to simplify the process, thereby reducing preparation steps and preparation costs. In addition, the preparation process may be easily managed by preparing the PI3K inhibitor under mild reaction conditions.

The invention claimed is:

1. A method for preparing a compound of formula 7, the method comprising:

(S1) preparing a compound of formula 5 from a compound of formula 4;

(S2) reacting the compound of formula 5 with dimethylformamide-dimethylacetal to prepare a compound of formula 6; and (S3) subjecting the compound of formula 6 to a cyclization reaction to prepare the compound of formula 7:

[Formula 4]

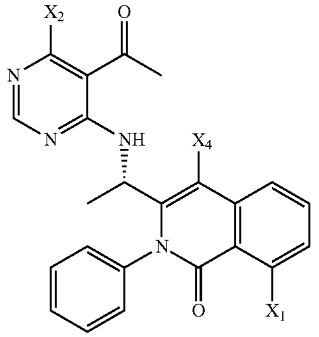

[Formula 5]

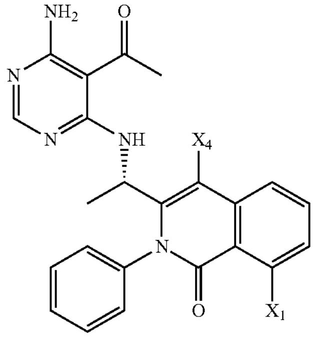

[Formula 6]

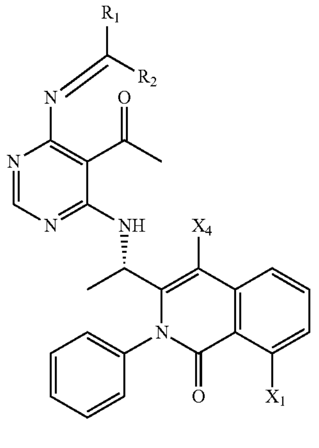

-continued

[Formula 7]

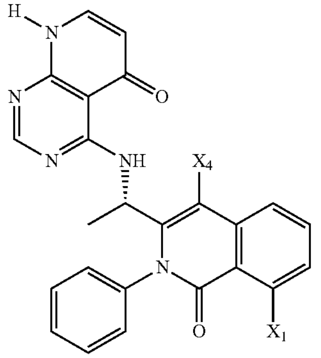

wherein in above formulas 4 to 7, $X_1$, $X_2$ and $X_4$ are each independently a halogen atom, and in above formula 6, any one of $R_1$ and $R_2$ is a hydrogen atom and other is dimethylamine, and wherein above (S2) is performed in a polar aprotic solvent.

2. The method of claim 1, further comprising:

(S1-1) subjecting a compound of formula 3 to a halogenation reaction to prepare the compound of formula 4:

[Formula 3]

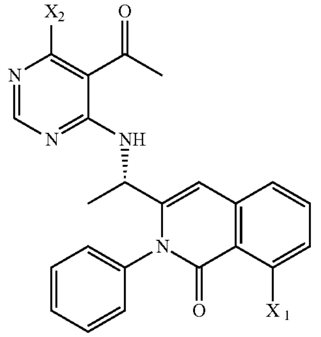

wherein in above formula 3, $X_1$ and $X_2$ are each independently same as defined in above formulas 4 to 7.

3. The method of claim 2, further comprising:

(S1-2) reacting a compound of formula 1 with a compound of formula 2 to prepare the compound of above formula 3:

[Formula 1]

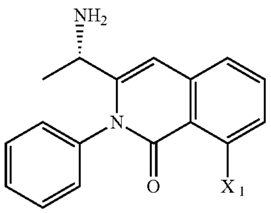

[Formula 2]

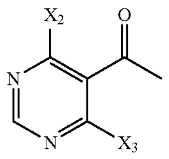

wherein in above formulas 1 and 2, $X_1$ and $X_2$ are each independently same as defined in above formulas 4 to 7, and in above formula 2, $X_3$ is a halogen atom.

4. The method of claim 1, wherein above (S1) is performed under a basic condition.

5. The method of claim 1, wherein above (S1) is performed in a polar aprotic solvent.

6. The method of claim 2, wherein above (S1-1) is reacting the compound of above formula 3 with N-chlorosuccinimide to perform a chlorination reaction.

7. The method of claim 1, wherein above (S1) comprises reacting the compound of above formula 4 with ammonium hydroxide to produce a crude product of formula 5.

8. The method of claim 7, wherein above (S1) comprises purifying the crude product.

9. The method of claim 8, wherein the purifying of the crude product uses at least one solvent selected from the group consisting of ethanol, isopropyl alcohol, and acetone, as a purification solvent.

10. The method of claim 8, wherein in the purifying of the crude product, isopropyl alcohol is used as the purification solvent.

11. The method of claim 1, wherein in above (S3), the cyclization reaction comprises reacting the compound of above formula 6 with a base and adding an acid.

12. The method of claim 11, wherein the base is a tert-butoxide salt.

13. The method of claim 11, wherein the acid is acetic acid or hydrochloric acid.

14. A method for preparing a compound of formula 6, the method comprising:

reacting a compound of formula 5 with dimethylformamide-dimethylacetal in a polar aprotic solvent:

[Formula 5]

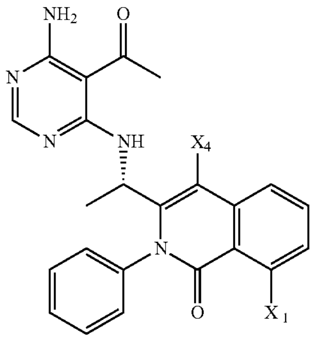

[Formula 6]

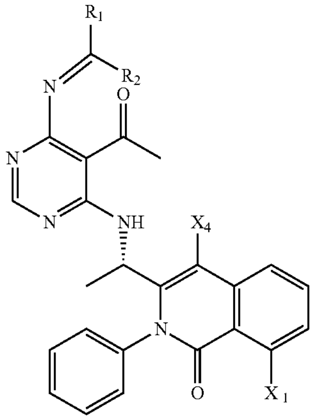

wherein in above formulas 5 and 6, $X_1$ and $X_4$ are each independently a halogen atom, and in above formula 6, any one of $R_1$ and $R_2$ is a hydrogen atom and other is dimethylamine.

15. A method for preparing a compound of formula 7, the method comprising:

subjecting a compound of formula 6 to a cyclization reaction:

[Formula 6]

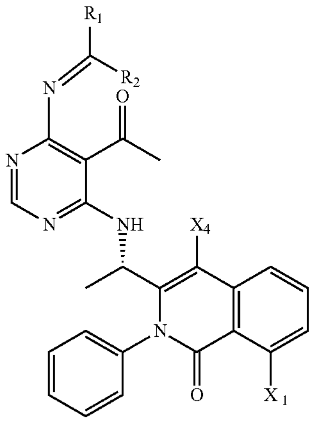

[Formula 7]

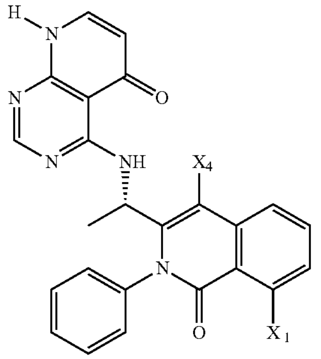

wherein in above formulas 6 and 7, $X_1$ and $X_4$ are each independently a halogen atom, and in above formula 6, any one of $R_1$ and $R_2$ is a hydrogen atom and other is dimethylamine.

16. A compound represented by formula 6 below:

[Formula 6]

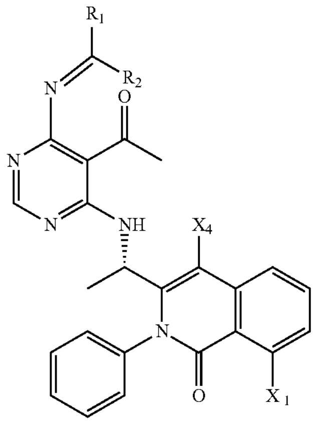

wherein in above formula 6, $X_1$ and $X_4$ are each independently a halogen atom, and any one of $R_1$ and $R_2$ is a hydrogen atom and other is dimethylamine.

17. The method of claim 1, wherein in above (S2), the polar aprotic solvent is dichloromethane.

* * * * *